United States Patent [19]

Becker et al.

[11] Patent Number: 5,608,113

[45] Date of Patent: Mar. 4, 1997

[54] PROCESS FOR PREPARATION OF DIAMINES BY CATALYTIC AMINATION OF AMINOALCOHOLS

[75] Inventors: Rainer Becker, Bad Dürkheim; Volkmar Menger, Neustadt; Wolfgang Reif, Frankenthal; Andreas Henne, Neustadt, all of Germany

[73] Assignee: BASF Aktiengesellschaft, Ludwigshafen, Germany

[21] Appl. No.: 513,632

[22] Filed: Aug. 10, 1995

[30] Foreign Application Priority Data

Aug. 19, 1994 [DE] Germany .......................... 44 29 547.2

[51] Int. Cl.$^6$ .............................................. C07C 209/16
[52] U.S. Cl. .......................................... 564/480; 564/479
[58] Field of Search ................................... 564/479, 480

[56] References Cited

U.S. PATENT DOCUMENTS

| | | | |
|---|---|---|---|
| 4,014,933 | 3/1977 | Boettger et al. | 260/563 |
| 4,151,204 | 4/1979 | Ichikawa et al. | 502/331 |
| 4,891,349 | 1/1990 | Bowman | 564/480 |
| 5,002,922 | 3/1991 | Irgang et al. | 260/584 |
| 5,166,433 | 11/1992 | Irgang et al. | 564/480 |

FOREIGN PATENT DOCUMENTS

| | | |
|---|---|---|
| 696572 | 2/1986 | European Pat. Off. . |
| 382049 | 12/1991 | European Pat. Off. . |
| 254335 | 1/1992 | European Pat. Off. . |
| 514692 | 11/1992 | European Pat. Off. . |
| 1953263 | 2/1972 | Germany . |

*Primary Examiner*—Brian M. Burn
*Assistant Examiner*—Lily Ledynh
*Attorney, Agent, or Firm*—Keil & Weinkauf

[57] ABSTRACT

In a process for preparing diamines from aminoalcohols and nitrogen compounds selected from the group consisting of ammonia and primary and secondary amines at from 80° to 250° C. and pressures of from 1 to 400 bar using hydrogen in the presence of a zirconium, copper, nickel catalyst, the catalytically active composition comprises from 20 to 85% by weight of oxygen-containing zirconium compounds, calculated as $ZrO_2$, from 1 to 30% by weight of oxygen-containing compounds of copper, calculated as CuO, from 30 to 70% by weight of oxygen-containing compounds of nickel, calculated as NiO, from 0.1 to 5% by weight of oxygen-containing compounds of molybdenum, calculated as $MoO_3$, and from 0 to 10% by weight of oxygen-containing compounds of aluminum and/or manganese, calculated as $Al_2O_3$ and $MnO_2$ respectively.

10 Claims, No Drawings

PROCESS FOR PREPARATION OF DIAMINES BY CATALYTIC AMINATION OF AMINOALCOHOLS

The present invention relates to a process for the catalytic amination of aminoalcohols using nitrogen compounds and hydrogen in the presence of a zirconium, copper, nickel catalyst at elevated temperatures and pressures, using zirconium, copper, nickel catalysts whose active composition contains oxygen-containing compounds of molybdenum.

DE-A-19 53 263 discloses the preparation of amines by the hydrogenative amination of the corresponding alcohols over catalysts containing cobalt, nickel and copper. In these catalysts, aluminum or silicon dioxide is used as support material. These catalysts enable good conversions to be obtained at high temperatures and pressures. If the reaction is carried out at lower temperatures and pressures, the conversion and selectivity are greatly reduced.

EP-A-254 335 discloses Ni-Co-Ru catalysts on aluminum oxide or silicon dioxide supports, which catalysts additionally contain halides in their active composition, for the hydrogenative amination of alcohols. These catalysts give yields of only 61% at most at 200° C. and 55 bar.

U. S. Pat. No. 4,151,204 discloses catalysts for preparing aminoalcohols, which catalysts comprise a metal such as cobalt, nickel or copper, preferably nickel or cobalt, and may be undoped or doped with small amounts of zirconium, with the zirconium being added in a molar ratio of from 0.005 : 1 to 0.2: 1, based on the nickel or cobalt. Higher zirconium contents lead to secondary reactions such as the decomposition of the products.

EP-A-382 049 discloses catalysts and processes for the hydrogenative amination of alcohols. These catalysts, whose active composition comprises oxygen-containing zirconium, copper, cobalt and nickel compounds, do have good activity and selectivity, but have operating lives which warrant improvement.

It is an object of the present invention to overcome said disadvantages.

We have found that this object is achieved by a novel, improved process for preparing diamines from aminoalcohols and nitrogen compounds selected from the group consisting of ammonia and primary and secondary amines at;from 80° to 250° C. and pressures of from 1 to 400 bar using hydrogen in the presence of a zirconium, copper, nickel catalyst, wherein the catalytically active composition comprises from 20 to 85% by weight of oxygen-containing zirconium compounds, calculated as $ZrO_2$, from 1 to 30% by weight of oxygen-containing compounds of copper, calculated as CuO, from 30% to 70% by weight of oxygen-containing compounds of nickel, calculated as NiO, from 0.1 to 5% by weight of oxygen-containing compounds of molybdenum, calculated as $MoO_3$, and from 0 to 10% by weight of oxygen-containing compounds of aluminum and/or manganese, calculated as $Al_2O_3$ and $MnO_2$ respectively. Preference is given to preparing diamines of the general formula I

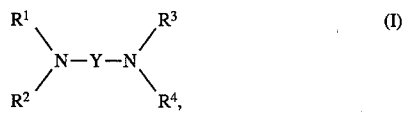

where $R^1, R^2, R^3, R^4$ are $C_1$- to $C_{20}$-alkyl, $C_3$- to $C_{12}$-cycloalkyl, aryl, $C_7$- to $C_{20}$-aralkyl and $C_7$- to $C_{20}$-alkylaryl or together $(CH_2)_n-X-(CH_2)_m$, $R^1, R^2$ can also be hydrogen, $R^5$ is hydrogen, $C_1$- to $C_{20}$-alkyl, $C_3$- to $C_{12}$-cycloalkyl, aryl, $C_7$- to $C_{20}$-aralkyl and $C_7$- to $C_{20}$-alkylaryl, is oxygen, $CH_2$ or $N-R^5$, Y is a $C_2$- to $C_{12}$-alkylene chain which may be unsubstituted or monosubstituted to pentasubstituted by $C_1$- to $C_4$-alkyl, n, m are integers from 1 to 4, from aminoalcohols of the general formula II

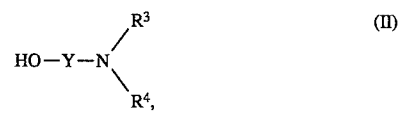

and nitrogen compounds of the general formula III

where $R^1, R^2, R^3, R^4, R^5$, X, Y and the indices n and m are as defined above.

Suitable aminoalcohols are virtually all primary and secondary aliphatic aminoalcohols. The aliphatic aminoalcohols can be linear, branched or cyclic. Secondary aminoalcohols are aminated the same as primary aminoalcohols. No restrictions are hitherto known on the number of carbon atoms in the aminatable aminoalcohols. The aminoalcohols can also bear substituents which are inert under the conditions of the hydrogenated amination.

Preference is given to aminating, for example, the following aminoalcohols:

N,N-dimethylaminoethanol, N,N-diethylaminoethanol, N,N-di-n-propylaminoethanol, N,N-di-iso-propylaminoethanol, N,N-di-n-butylaminoethanol, N,N-di-iso-butylaminoethanol, N,N-di-sec-butylaminoethanol, N,N-di-tert-butylaminoethanol, N,N-dimethylaminopropanol, N,N-diethylaminopropanol, N,N-di-n-propylaminopropanol, N,N-di-iso-propylaminopropanol, N,N-di-n-butylaminopropanol, N,N-di-iso-butylaminopropanol, N,N-di-sec-butylaminopropanol, N,N-di-tert-butylaminopropanol, dimethylaminopentan-4-ol and diethylaminopentan-4-ol.

Suitable aminating agents in the hydrogenative amination of aminoalcohols are ammonia or primary or secondary, aliphatic or cycloaliphatic amines.

If ammonia is used as aminating agent, the alcohol hydroxyls are first converted into free amino groups (-NH2). The primary amines thus formed can react with further alcohol to give the corresponding secondary amines and these can in turn react with further alcohol to give the corresponding, symmetric tertiary amines. Depending on the composition of the reaction mixture and the reaction conditions used, viz. pressure, temperature, reaction time, this method can be used to prepare primary, secondary or tertiary amines as desired.

Primary or secondary amines can, like ammonia, be used as aminating agent.

Preference is given to using, for example, the following monoalkylamines and dialkylamines as aminating agent: methylamine, dimethylamine, ethylamine, diethylamine, propylamine, diisopropylamine, butylamine, pentylamine, hexylamine and cyclohexylamine.

The aminating agent can be used in a stoichiometric amount based on the alcohol hydroxyl to be aminated. However, preference is given to using an excess of aminating agent, generally a greater than 5 molar excess per mole of alcohol hydroxyl to be aminated. Ammonia specifically is generally used in a from 1.5 to 250-fold, preferably from 5 to 100-fold, in particular from 10 to 50-fold, molar excess per mole of alcohol hydroxyls to be reacted. Higher excesses both of ammonia and of primary or secondary amines are possible.

The hydrogen is generally fed into the reaction in an amount of from 5 to 400 standard 1, preferably in an amount of from 50 to 200 standard 1, per mole of alcohol component.

The reaction is generally carried out without additional solvent. In the reaction of high molecular weight starting compounds which are highly viscous or solid at room temperature, it can be advantageous to use a solvent which is inert under the reaction conditions, such as tetrahydrofuran, dioxane, N-methylpyrrolidone or ethylene glycol dimethyl ether.

The reaction is usually carried out at from 80° to 250° C., preferably from 120° to 230° C., particularly preferably from 130° to 200° C. In general, it is carried out at a pressure of from 1 to 400 bar, but preference is given to using pressures of from 10 to 250 bar, in particular from 30 to 200 bar.

It is possible to use higher temperatures and a higher total pressure. The total pressure in the reaction vessel, which is made up of the sum of the partial pressures of the aminating agent, the alcohol component and the reaction product formed, as well as that of any solvent used, at the given temperatures, is advantageously set by pressurization with hydrogen to the desired reaction pressure.

For the selectivity of the present process it can be advantageous to mix the catalyst elements in the reactor with inert packing elements, ie. to "dilute" them. The proportion of the packing elements in such catalyst preparations can be from 20 to 80, particularly from 30 to 60 and most particularly from 40 to 50, parts by volume.

In practice, the reaction is generally carried out by simultaneously feeding the alcohol and the aminating agent to the catalyst, which is usually located in a fixed-bed reactor preferably heated externally, at the desired reaction temperature and the desired pressure. The space velocity over the catalyst is generally from 0.02 to 3 1, preferably from 0.05 to 2 1 and particularly preferably from 0.1 to 1.6 1, of alcohol per liter of catalyst and hour. It is advantageous to heat the reactants, preferably to the reaction temperature, before feeding them into the reaction vessel.

The reactor can be operated either in the upward flow mode or in the downward flow mode, ie. the reactants can be passed through the reactor either upwards from the bottom or downwards from the top. It is self-evident that the process can be carried out either batchwise or continuously. In both cases, the excess aminating agent can be circulated together with the hydrogen. If the conversion in the reaction is incomplete, the unreacted starting material can likewise be recycled to the reaction zone.

After the material discharged from the reaction has advantageously been depressurized, the excess aminating agent and the hydrogen are removed therefrom and the aminated products obtained are purified by distillation, liquid extraction or crystallization. The excess amination agent and the hydrogen are advantageously recycled to the reaction zone. The same applies to any unreacted or incompletely reacted alcohol component.

The water of reaction formed in the course of the reaction generally does not adversely affect the degree of conversion, the reaction rate, the selectivity and the catalyst life and is therefore advantageously removed from the reaction product only in the distillative workup of this product.

In general, the catalysts of the invention are preferably used in the form of unsupported catalysts which, unlike supported catalysts, consist entirely of catalytically active composition. Unsupported catalysts can be employed by introducing the catalytically active, pulverized composition into the reaction vessel, or by arranging the catalytically active composition in the reactor, after milling, mixing with forming aids, shaping and heat treatment, as shaped catalyst elements, for example as spheres, cylinders, rings, spirals.

The catalytically active composition of the catalysts of the invention contains not only oxygen-containing compounds of zirconium, but also oxygen-containing compounds of nickel, copper and molybdenum.

Since the concentrations stated are each based, unless otherwise indicated, on the catalytically active mass of the catalyst, the catalytically active mass of the catalyst is hereinafter defined as the sum of the masses of the catalytically active constituents zirconium, nickel, copper and molybdenum in the catalyst, in each case calculated as $ZrO_2$, $NiO$, $CuO$ or $MoO_3$, after the catalyst has undergone its last heat treatment and before it is reduced with hydrogen.

In general the zirconium oxide content of the catalysts of the invention is from 20 to 85% by weight, preferably from 25 to 60% by weight.

The other components nickel, copper and molybdenum are generally present in the catalytically active composition in a total amount of from 15 to 80% by weight, preferably from 30 to 70% by weight, in particular from 50 to 70% by weight. The catalytically active composition of preferred catalysts comprises from 20 to 85% by weight, preferably from 25 to 60% by weight, of oxygen-containing zirconium compounds, from 1 to 30% by weight, preferably from 10 to 25% by weight, of oxygen-containing copper compounds, from 30 to 70% by weight, preferably from 40 to 70% by weight, particularly preferably from 45 to 60% by weight, of oxygen-containing compounds of nickel, from 0.1 to 5% by weight, preferably from 0.5 to 3.5% by weight, of oxygen-containing compounds of molybdenum and from 0 to 10% by weight of oxygen-containing compounds of aluminum and/or manganese.

Various methods can be used for preparing the unsupported catalysts. They can be obtained, for example, by mixing pulverulent mixtures of the hydroxides, carbonates, oxides and/or other salts of the components zirconium, cobalt, nickel and copper with water and subsequently extruding and heat-treating the composition thus obtained.

However, precipitation methods are generally used for preparing the catalysts of the invention. Thus, for example, they can be obtained by coprecipitation of the cobalt, nickel and copper components from an aqueous salt solution containing these elements by means of mineral bases in the presence of a slurry of a sparingly soluble, oxygen-containing zirconium compound and subsequent washing, drying and calcination of the precipitate obtained. Sparingly soluble, oxygen-containing zirconium compounds which can be used are, for example, zirconium dioxide, zirconium oxide hydrate, zirconium phosphates, borates and silicates. The slurries of the sparingly soluble zirconium compounds can be prepared by suspending fine powders of these compounds in water with vigorous stirring; they are advantageously obtained by precipitating the sparingly soluble zirconium compounds from aqueous zirconium salt solutions by means of mineral bases.

The catalysts of the invention are preferably prepared by coprecipitation of all their components. For this purpose, it is advantageous to heat an aqueous salt solution containing the catalyst components and, while stirring, add an aqueous mineral base, in particular an alkali metal base such as sodium carbonate, sodium hydroxide, potassium carbonate or potassium hydroxide, until precipitation is complete. The type of salts used is generally not critical: since this procedure depends primarily on the water-solubility of the salts, a criterion is good water-solubility so as to be able to prepare these relatively highly concentrated salt solutions. It should be self-evident that, in the selection of the salts of the individual components, the salts selected should have anions which do not interfere, whether by causing undesired precipitations or by forming complexes so as to hinder or prevent the precipitation.

Catalysts of the invention having particularly advantageous properties can be obtained by separately precipitating a part of the zirconium component of the catalyst, advantageously from an aqueous zirconium salt solution, in a precipitation apparatus by adding aqueous mineral bases. The zirconium oxide hydrate thus obtained, preferably freshly precipitated, can then have the remainder of the zirconium component of the catalyst together with the other catalytically active components precipitated onto it in a coprecipitation, as described above. It is here generally particularly advantageous to preprecipitate from 10 to 80% by weight, preferably from 30 to 70% by weight and particularly preferably from 40 to 60% by weight, of the total amount of zirconium in the catalytically active composition.

The precipitates obtained in these precipitation reactions are generally chemically non-uniform and comprise, inter alia, mixtures of the oxides, oxide hydrates, hydroxides, carbonates and insoluble and basic solvents of the metals concerned. The filterability of the precipitates may be improved by ageing them, i.e. leaving them to stand for some time after precipitation, if desired while being kept hot or while passing in air.

The precipitates obtained by these precipitation methods are processed into the catalysts of the invention using customary methods. After washing, they are generally dried at from 80° to 200° C., preferably at from 100° to 150° C., and then calcinated. The calcination is generally carried out at from 300° to 800° C., preferably at from 400° to 600° C., in particular at from 450° to 550° C.

After the calcination, the catalyst is advantageously conditioned, either by bringing it to a particular particle size by milling or by, after milling, mixing it with forming aids such as graphite or stearic acid, pressing it into shaped compacts by means of a tableting press and heat treating the resultant compacts. The heat-treatment temperatures here generally correspond to the temperatures in the calcination.

The catalysts prepared in this way contain the catalytically active metals in the form of a mixture of their oxygen-containing compounds, ie. in particular as oxides and mixed oxides.

The catalysts prepared in this way are stored and, if necessary handled, as such. Before being used as catalysts for the hydrogenative amination of alcohols, they are usually prereduced. However, they can also be used without prereduction, in which case they are reduced under the conditions of the hydrogenative amination by the hydrogen present in the reactor. For the prereduction, the catalysts are generally first exposed to a nitrogen/hydrogen atmosphere at from 150° to 200° C. for from 12 to 20 hours and subsequently treated in a hydrogen atmosphere at from 200° to 300° C. for a further period of up to 24 hours. In this prereduction, part of the oxygen-containing metal compounds present in the catalysts are reduced to the corresponding metals, so that these are present together with the various oxygen compounds in the active form of the catalyst.

The substituents $R^1$, $R^2$, $R^3$, $R^4$, $R^5$, X, Y and the indices m and n in the compounds I, II and III are, independently of one another, as defined below:

$R^1$, $R^2$, $R^3$, $R^4$, $R^5$ $C_1$- to $C_{20}$-alkyl, preferably $C_1$- to $C_8$-alkyl such as methyl, ethyl, n-propyl, iso-propyl, n-butyl, iso-butyl, sec-butyl, tert-butyl, n-pentyl, iso-pentyl, sec-pentyl, neo-pentyl, 1,2-dimethylpropyl, n-hexyl, iso-hexyl, sec-hexyl, n-heptyl, iso-heptyl, n-octyl, iso-octyl, 2-ethylhexyl, particularly preferably $C_1$- to $C_4$-alkyl such as methyl, ethyl, n-propyl, iso-propyl, n-butyl, iso-butyl, sec-butyl, tert-butyl, $C_3$- to $C_{12}$-cycloalkyl, preferably $C_3$- to $C_8$-cycloalkyl such as cyclopropyl, cyclobutyl, cyclopentyl, cyclohexyl, cycloheptyl and cyclooctyl, particularly preferably cyclopentyl, cyclohexyl and cyclooctyl, aryl such as phenyl, 1-naphthyl, 2-naphthyl, 1-anthryl, 2-anthryl and 9-anthryl, preferably phenyl, 1-naphthyl and 2-naphthyl, particularly preferably phenyl, $C_7$- to $C_{20}$-alkylaryl, preferably $C_7$- to $C_{12}$-alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-tri-methylphenyl, 2-ethylphenyl, 3-ethylphenyl, 4-ethylphenyl, 2-n-propylphenyl, 3-n-propylphenyl and 4-n-propylphenyl, $C_7$- to $C_{20}$-aralkyl, preferably $C_7$- to $C_{12}$-phenylalkyl such as benzyl, 1-phenethyl, 2-phenethyl, 1-phenylpropyl, 2-phenylpropyl, 3-phenyl-propyl, 1-phenylbutyl, 2-phenyl-butyl, 3-phenyl-butyl and 4-phenylbutyl, particularly preferably benzyl, 1-phenethyl and 2-phenethyl, $R^1$ and $R^2$ together a $-(CH_2)_1-X-(CH_2)_m$ group, $R^1$, $R^2$, $R^5$
  hydrogen, 5 X
  oxygen,
  $CH_2$
  $N-R^5$, Y
  a $C_2$- to $C_{12}$-alkylene chain which may be unsubstituted or monosubstituted to pentasubstituted by $C_1$- to $C_4$-alkyl, for example $(CH_2)_2$, $(CH_2)_3$, $(CH_2)_4$, $(CH_2)_5$, $(CH_2)_6$, $(CH_2)_7$, $(CH_2)_8$, $(CH_2)_9$, $(CH_2)_{10}$, $(CH_2)_{11}$, $(CH_2)_{12}$, $CH(CH_3)CH_2$, $CH_2CH(CH_3)CH_2$, $CH_2CH_2CH$ $(CH_3)$ and $CH_2CH_2CH_2CH$ $(CH_3)$, preferably a $C_2$- to $C_8$-alkylene chain which may be unsubstituted or monosubstituted to trisubstituted by methyl or ethyl, for example $(CH_2)_2$, $(CH_2)_3$, $(CH_2)_4$, $(CH_2)_5$, $(CH_2)_6$, $(CH_2)_7$, $(CH_2)_8$, $CH(CH_3)CH_2$, $CH_2CH(CH_3)CH_2$, $CH_2CH_2CH$ $(CH_3)$ and $CH_2CH_2CH_2CH(CH_3)$, particularly preferably a $C_2$- to $C_6$-alkylene chain which may be unsubstituted or monosubstituted to trisubstituted by methyl, for example $(CH_2)_2$, $(CH_2)_3$, $(CH_2)_4$, $(CH_2)_5$, $(CH_2)_6$, $CH(CH_3)CH_2$, $CH_2CH(CH_3)CH_2$, $CH_2CH_2CH(CH_3)$ and $CH_2CH_2CH_2CH(CH_3)$, n, m
  an integer from 1 to 4, preferably an integer from 1 to 3, particularly preferably 1 or 2.

The diamines obtainable according to the invention are suitable, inter alia, as intermediates in the production of fuel additives (U.S. Pat. No. 3,275,554; DE-A-21 25 039 and DE-A-36 11 230), surfactants, drugs and crop protection agents and of vulcanization accelerators.

EXAMPLES

Catalyst Preparation

Preparation of catalyst A

An aqueous solution of nickel nitrate, copper nitrate and zirconium acetate, containing 4.48% of NiO, 1.52% of CuO and 2.82% of $ZrO_2$, was precipitated by mixing constant streams of this solution and a 20% strength aqueous sodium carbonate solution in a stirred vessel at 70° C., in such a way that the pH measured using a glass electrode was kept at 7.0.

The suspension obtained was filtered and the filtercake was washed with deionized water until the electrical conductivity of the filtrate was about 20 µS. The filtercake, while still moist, was then mixed with sufficient ammonium heptamolybdate for the oxide mixture indicated below to be obtained. The filtercake was then dried at 150° C. in a drying oven or a spray dryer. The hydroxide-carbonate mixture obtained in this way was then heat treated at 500° C. for 4 hours.

The catalyst obtained had the composition:

50% by weight of NiO, 17% by weight of CuO, 1.5% by weight of $MoO_3$ and 31.5% by weight of $ZrO_2$. The catalyst powder was mixed with by weight of graphite and shaped into 6×3 mm pellets. The pellets had a porosity (measured by water absorption) of 0.20 ml/g and a hardness of 3500 N/cm².

EXAMPLE 1

Amination of 1-diethylaminopentan-4-ol

A continuously operated high-pressure reactor was charged with 700 ml of the catalyst A. For the amination of the diethylaminopentan-4-ol, the conditions shown in the table below were set and the crude product analyses likewise recorded were obtained (pressure constant at 200 bar)

| Temp. [°C.] | Space velocity*) | Molar ratio alcohol:$NH_3$ | Conversion [%] | Selectivity**) [%] |
|---|---|---|---|---|
| 180 | 0.42 | 1:20 | 97 | 80 |
| 180 | 0.84 | 1:20 | 91 | 90 |
| 170 | 0.42 | 1:20 | 84 | 90 |
| 170 | 0.62 | 1:20 | 68 | 93 |
| 160 | 0.31 | 1:20 | 70 | 94 |
| 160 | 0.2 | 1:20 | 73 | 94 |
| 165 | 0.2 | 1:20 | 78 | 90 |
| 165 | 0.2 | 1:10 | 68 | 82 |
| 165 | 0.2 | 1:30 | 82 | 91 |
| 165 | 0.2 | 1:40 | 83 | 92 |
| 165 | 0.2 | 1:5 | 65 | 63 |

*)velocity: kg alkohol/l cat · h

**)selectivity = $\frac{\text{yield of diethylaminopentylamine}}{\text{conversion of diethylaminopentanol}} \cdot 100$ The results show that, under suitable conditions, selectivities of >90% can be obtained. The experiment was carried out over a total of 150 days when the catalyst was removed from the reactor after this time it showed no signs of disintegration.

EXAMPLE 2

Scale-up experiment for the amination of 1-diethylaminopentan-4-ol

A continuously operated high-pressure reactor is charged with 60 l of catalyst (type A) and fed with 15 l/h of diethylaminopentanol and 40 l of ammonia (corresponding to a molar ratio of 1:20) at 200 bar and 155°–157° C. in the upward flow mode. The material discharged from the reactor showed a selectivity for the desired product of 91% at a conversion of 80%.

We claim:

1. A process for preparing diamines from aminoalcohols and nitrogen compounds selected from the group consisting of ammonia and primary and secondary amines at from 80° to 250° C. and pressures of from 1 to 400 bar using hydrogen in the presence of a zirconium, copper, nickel catalyst, wherein the catalytically active composition comprises from 20 to 85% by weight of oxygen-containing zirconium compounds, calculated as $ZrO_2$, from 1 to 30% by weight of oxygen-containing compounds of copper, calculated as CuO, from 30 to 70% by weight of oxygen-containing compounds of nickel, calculated as NiO, from 0.1 to 5% by weight of oxygen-containing compounds of molybdenum, calculated as $MoO_3$, and from 0 to 10% by weight of oxygen-containing compounds of aluminum and/or manganese, calculated as $Al_2O_3$ and $MnO_2$ respectively.

2. A process for preparing diamines of the general formula I

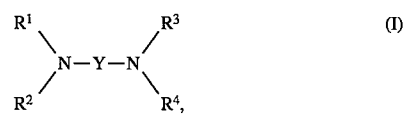

where $R^1, R^2, R^3, R^4$ are $C_1$- to $C_{20}$-alkyl, $C_3$- to $C_{12}$-cycloalkyl, aryl, $C_7$- to $C_{20}$-aralkyl and $C_7$- to $C_{20}$-alkylaryl or together $(CH_2)_n$—X—$(CH_2)_m$, $R^1, R^2$ can also be hydrogen, $R^5$ is hydrogen, $C_1$- to $C_{20}$-alkyl, $C_3$- to $C_{12}$-cycloalkyl, aryl, $C_7$- to $C_{20}$-aralkyl and $C_7$- to $C_{20}$-alkylaryl, X is oxygen, $CH_2$ or N—$R^5$, Y is a $C_2$- to $C_{12}$-alkylene chain which may be unsubstituted or monosubstituted to pentasubstituted by $C_1$- to $C_4$-alkyl, n, m are integers from 1 to 4, from aminoalcohols of the general formula II

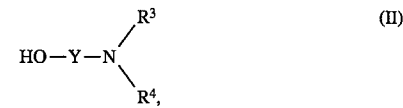

and nitrogen compounds of the general formula III

where $R^1, R^2, R^3, R^4, R^5$, X, Y and the indices n and m are as defined above, at from 80° to 250° C. and pressures of from 1 to 400 bar using hydrogen in the presence of a zirconium, copper, nickel catalyst, wherein the catalytically active composition comprises from 20 to 85% by weight of oxygen-containing zirconium compounds, calculated as $ZrO_2$, from 1 to 30% by weight of oxygen-containing compounds of copper, calculated as CuO, from 30 to 70% by weight of oxygen-containing compounds of nickel, calculated as NiO, from 0.1 to 5% by weight of oxygen-containing compounds of molybdenum, calculated as $MoO_3$, and from 0 to 10% by weight of oxygen-containing compounds of aluminum and/or manganese, calculated as $Al_2O_3$ and $MnO_2$ respectively.

3. A process for preparing diamines from aminoalcohols and nitrogen compounds using hydrogen in the presence of a zirconium, copper, nickel catalyst as claimed in claim 1, wherein the catalytically active composition comprises from 40 to 70% by weight of oxygen-containing compounds of nickel, calculated as NiO.

4. A process for preparing diamines from aminoalcohols and nitrogen compounds using hydrogen in the presence of a zirconium, copper, nickel catalyst as claimed in claim 1, wherein the catalytically active composition comprises from 45 to 60% by weight of oxygen-containing compounds of nickel, calculated as NiO.

5. A process for preparing diamines from aminoalcohols and nitrogen compounds using hydrogen in the presence of a zirconium, copper, nickel catalyst as claimed in claim 1, wherein the catalytically active composition comprises from 0.5 to 3.5% by weight of oxygen-containing compounds of molybdenum, calculated as $MoO_3$.

6. A process for preparing diamines from aminoalcohols and nitrogen compounds using hydrogen in the presence of a zirconium, copper, nickel catalyst as claimed in claim 1, wherein the catalytically active composition comprises from 25 to 60% by weight of oxygen-containing zirconium compounds, calculated as $ZrO_2$.

7. A process for preparing diamines from aminoalcohols and nitrogen compounds using hydrogen in the presence of a zirconium, copper, nickel catalyst as claimed in claim 1, wherein the catalytically active composition comprises from 10 to 25% by weight of oxygen-containing compounds of copper, calculated as CuO.

8. A process for preparing diamines from aminoalcohols and nitrogen compounds using hydrogen in the presence of a zirconium, copper, nickel catalyst as claimed in claim 1, wherein the reaction is carried out at from 120° to 230° C.

9. A process for preparing diamines from aminoalcohols and nitrogen compounds using hydrogen in the presence of a zirconium, copper, nickel catalyst as claimed in claim 1, wherein the reaction is carried out at pressures of from 10 to 250 bar.

10. A process for preparing diamines from aminoalcohols and nitrogen compounds using hydrogen in the presence of a zirconium, copper, nickel catalyst as claimed in claim 1, wherein the reaction is carried out at pressures of from 30 to 220 bar.

* * * * *